United States Patent [19]

Simonian et al.

[11] Patent Number: 5,959,012

[45] Date of Patent: Sep. 28, 1999

[54] METHYL OXIRANE DIBENZOYLRESORCINOL UV ABSORBERS

[75] Inventors: Amy Kathleen Simonian, Gansevoort; Gregory Ronald Gillette, Clifton Park; James Edward Pickett, Schenectady, all of N.Y.

[73] Assignee: General Electric Company, Schenectady, N.Y.

[21] Appl. No.: 08/908,026

[22] Filed: Aug. 11, 1997

[51] Int. Cl.[6] .............................. C08K 5/13; C08K 5/15; C07D 317/00; C07B 303/48; C07C 49/786
[52] U.S. Cl. .......................... 524/335; 524/108; 524/111; 524/114; 549/453; 549/469; 549/559; 568/333
[58] Field of Search ....................... 524/114, 111, 524/335, 108; 568/333; 549/469, 559, 453

[56] References Cited

U.S. PATENT DOCUMENTS

| | | | |
|---|---|---|---|
| 2,831,026 | 4/1958 | Greminger et al. | 524/335 |
| 2,900,361 | 8/1959 | Havens | 568/333 |
| 3,094,506 | 6/1963 | Weinberg et al. | 568/333 |
| 4,054,551 | 10/1977 | Layer | 549/469 |
| 4,691,059 | 9/1987 | Mitra et al. | 568/333 |
| 4,774,344 | 9/1988 | Kelsey | 549/453 |
| 5,152,983 | 10/1992 | Nambudiry et al. | 549/469 |

*Primary Examiner*—Veronica P. Hoke
*Attorney, Agent, or Firm*—Noreen C. Johnson; Douglas E. Stoner

[57] ABSTRACT

An epoxylated DBR, dibenzoylresorcinol and various derivatives thereof have been prepared to show usefulness in coatings due to compatibility and solubility. Such coatings can be acrylics, epoxies, or silicone hardcoats which are thermally or photo cured thermoset, or thermoplastic coating materials in a variety of solvent types. The disclosed UV absorber also has the advantage of a higher molecular weight and lower volatility than DBR alone thus providing processing advantages.

15 Claims, No Drawings

METHYL OXIRANE DIBENZOYLRESORCINOL UV ABSORBERS

This invention relates to derivatives of dibenzoylresorcinol which are capable of absorbing ultraviolet light and to methods for making the compounds, and to coating compositions comprising the compounds. More particularly, the dibenzoylresorcinol compounds comprise dibenzoylresorcinol coupled with an epoxy (oxirane) group on a bridging methylene and derivatives thereof. The invention also relates to coating compositions containing the dibenzoylresorcinol compounds which when applied to thermoplastic resin articles reduce discoloration of resin resulting from exposure to ultra violet radiation.

BACKGROUND OF THE INVENTION

Thermoplastic substrates such as polycarbonates are generally characterized by advantageous properties which include clarity, high ductility, high heat deflection temperature, and dimensional stability. Many of these materials are transparent and some are suitable as replacements for glass in automotive, aerospace, and architectural applications. However, the resins often are susceptible to degradation by ultraviolet light evidenced by development of discoloration. This results in loss of transparency, mechanical degradation of the substrate and erosion of the substrate surface.

As thermoplastic substrates, such as polycarbonate, are applied to outdoor uses it becomes important to enhance ultraviolet radiation stability of the substrate. This is accomplished by treating the substrate surface with a weather resistant coating material, which contains ultraviolet light absorbing agents. Weather resistant coating systems can be prepared by incorporation of ultraviolet light absorbers, such as benzotriazoles and benzophenones, and hindered amine light stabilizers.

However, the ultraviolet light absorbing compounds, often referred to as UV absorbers, decompose or volatalize upon exposure to ultraviolet light thus losing the ability to protect and often causing loss of necessary properties. Prolonged exposure to sunlight, moisture and thermal cycling conditions can cause yellowing, delamination and formation of microcracks in the coating material, decreasing transparency. This leads to a degradation of the favorable properties of the thermoplastic substrate which the UV absorbers are originally employed to protect. Accordingly, there is an ongoing need to develop new and efficient UV absorbing compounds.

Certain 4,6-dibenzoylresorcinols (DBRs) have been found to be effective UV absorbers for haloethylene polymers. DBRs, as bulk additives, are described in U.S. Pat. Nos. 2,794,052 and 2,933,553. However, a drawback in current compositions of DBRs is their relatively low molecular weight, i.e., molecular weight less than or equal to about 400 daltons, which leads to volatility during processing of the thermoplastic substrates or cure of the coatings. This can result in contamination of the processing equipment. Efforts to increase the molecular weight of DBR by adding substituents can result in diluting the effectiveness of the UV absorber. There is a need for UV absorbers characterized by photostability and effectiveness of the DBR chromophore with low volatility.

SUMMARY OF THE INVENTION

Described herein is a group of novel UV absorber compounds derived from 2-(methyloxirane)-4,6-dibenzoylresorcinol and UV absorbing coating composition containing these compounds.

DETAILED DESCRIPTION OF THE INVENTION

Described herein are 2-(propyl)-4,6-dibenzoylresorcinols having oxygen substitution in the 2 and 3 positions of the propyl group, derivatives of DBR, which are useful as a UV absorber in polymethylmethacrylate compositions and other coating films. The oxygen substitution includes a 2-(methylepoxy) group which can be opened and modified to provide the derivatives described below.

Compounds IV and V result from a reaction of the epoxylated DBR in an acetone/water/acid solution with and without heat, respectively. These UV absorbers have been tested in PMMA films and found to be effective stabilizers for unstabilized polycarbonate films as shown by the reduced rate of photo-yellowing of polycarbonate observed when compounds I—V are included in a polymethylmethacrylate coating applied to the polycarbonate before exposure to a xenon arc.

The instant invention provides novel dibenzoylresorcinol compositions capable of absorbing ultraviolet light and methods of making the compositions. The novel dibenzoylresorcinol derivatives are compatible in coating compositions to improve the weatherability of thermoplastic substrates.

The instant invention is directed to novel methylene-bridged dibenzoylresorcinol derivatives having an oxirane group on the bridging 2-methyl moiety which are useful for absorbing ultraviolet light having the formula:

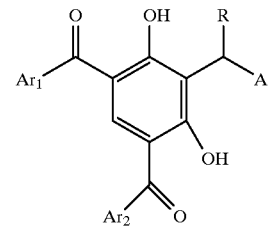

in which $Ar_1$ and $Ar_2$ are independently substituted or unsubstituted monocyclic or polycyclic aryl groups, R is hydrogen or an aliphatic group of from 1 to 8 carbons and A is an oxirane (epoxide) group. The oxirane can be ring opened to provide derivatives as described herein.

The UV absorbers of this invention are 2-(propyl)-4,6-dibenzoylresorcinols having oxygen substitution in the 2 and 3 positions of the propyl group.

The compounds of this invention and methods for making them are outlined in the following reaction diagram.

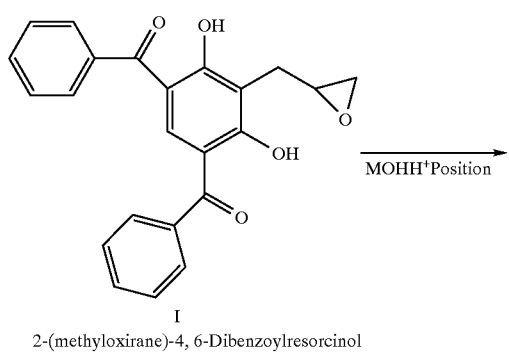
I
2-(methyloxirane)-4, 6-Dibenzoylresorcinol
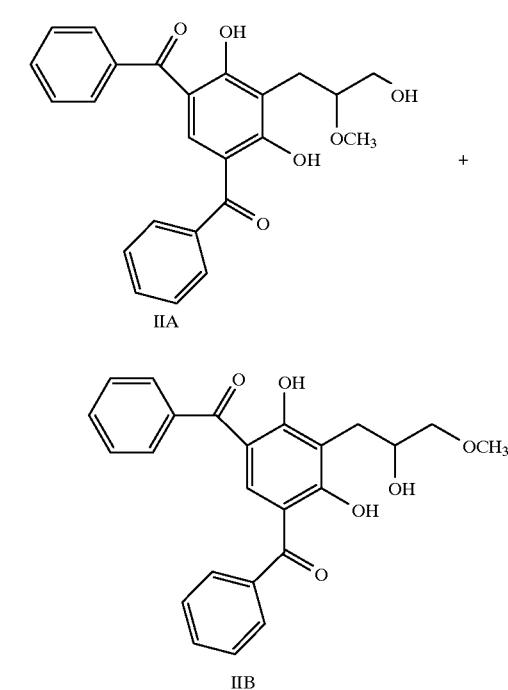
IIA
IIB
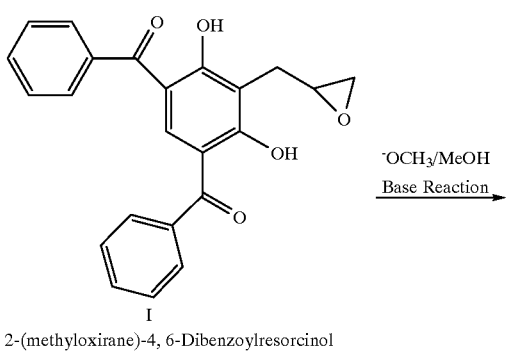
I
2-(methyloxirane)-4, 6-Dibenzoylresorcinol
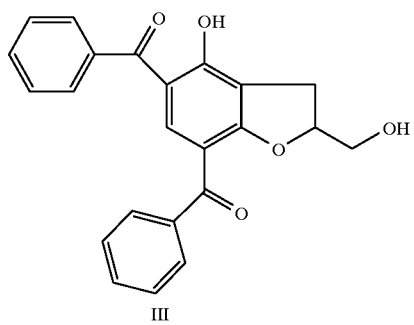
III
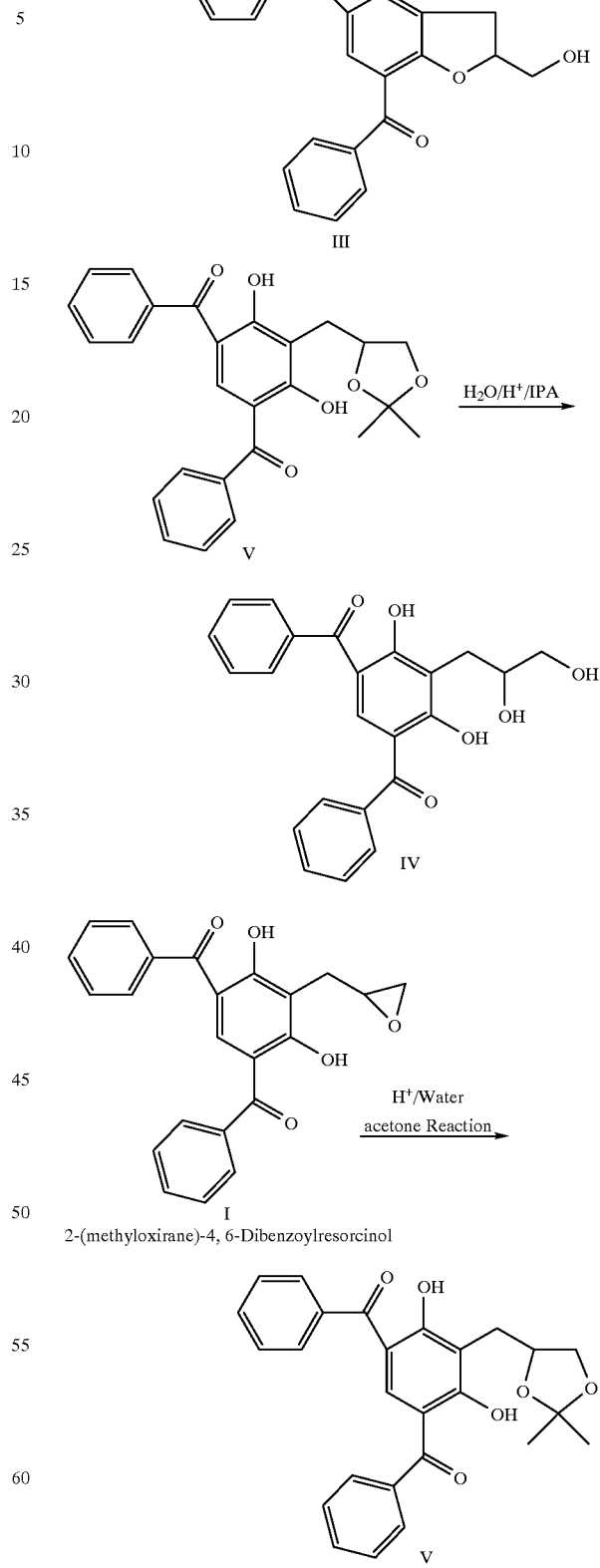

For convenience in the following description of the invention, the chemical names of these compounds are as follows:

I. 2-(methyloxirane)-4,6-dibenzoylrescorcinol,

IIA. 2-(3-hydroxypropyl)-4,6-dibenzoylrecorcinol,

IIIB. 2-(2-hydroxyl-3-methoxypropyl)-4,6-dibenzoylrecorcinol,

III. 2-hydroxymethyl-5-hydroxy-6,8-dibenzoyl-2,3-dihydrobenzofuran,

IV. 2-(2,3-dihydroxypropyl)-4,6-dibenzoylresorcinol, and

V. 2,2-dimethyl-5-[(2,6-dihydroxy-3,5-dibenzoylphenyl)methyl]-1,3-dioxolane.

The novel methylepoxy containing dibenzoylresorcinol derivatives described above can be incorporated into coating compositions by means known in the art. The coating compositions are defined as coatings comprising the methylepoxide dibenzoylresorcinol derivatives and a substantially transparent matrix composition. These compositions can be applied to protect polymers and articles from photo-induced decomposition of the polymer materials. Generally, the matrix material may contain acrylics, urethanes, melamines, or mixtures thereof.

The above-described coatings are applied to the surface of a solid substrate thus producing a coated solid substrate having resistance to ultraviolet light. Such coated solid substrates are often referred to as weatherable substrates. Generally, there are no limitations with respect to the thickness of the coatings applied to said solid substrates. They are, however, usually about 0.5 to about 50 μm thick and preferably about 3 to about 10 μm thick. In the instant invention, the solid substrates that may be employed often include polymer substrates such as acrylic polymers including poly(methyl methacrylate), polyesters such as poly(ethylene terephthalate) and poly(butylene terephthalate), polyamides, polyimides, acrylonitrile-styrene copolymers, styrene-acrylonitrile-butadiene copolymers, polyvinyl chloride, polystyrene, blends of polystyrene and polyphenylene ethers, butyrates, polyethylene and the like. Thermoplastic substrates can be with or without pigments. Moreover, said solid substrates may also include metal substrates, painted surfaces, glass, ceramics and textiles. However, the coating compositions of the instant invention are preferably employed to coat polycarbonates.

The preparation of the novel methylene-bridged dibenzoylresorcinol derivatives deriving from an oxirane group on the bridging methylene of the instant invention is further illustrated by the following examples. Molecular structures of all products in the examples may be confirmed by the proton and carbon-13 nuclear magnetic resonance spectroscopy and mass spectral analysis.

Olefin groups such as the allyl portion of 2-(allyl)-4,6-dibenzoylresorcinol can be epoxidized by various peracids of which meta-chloroperbenzoic acid is most often used. Amino and other groups affected by the reagent should not be present in the reactant molecule. Other peracids which can be used include peracetic acid, perbenzoic acid, trifluroperacetic acid, and 3,5-dinitroperoxybenzoic acid. In addition air oxidation in the presence of silver and heat can be employed.

The ultraviolet radiation absorbing compounds may be incorporated into any coating composition suitable for coating plastic substrates or articles such as polycarbonate articles. Preferred coating materials include thermoplastic acrylics and thermosetting acrylics and silicone hardcoats with the most preferred coating composition being polymethyl methacrylate and various co-polymers thereof.

The amount of ultraviolet absorbing compound present in the coating composition is defined as an effective amount to protect the underlying resins substrate against discoloration or degradation caused by ultraviolet radiation. Essentially, an effective amount of UV absorber is the amount necessary for the coating material to have an absorbance of at least about 0.3 at about 300 to 330 nm. This corresponds to absorption of at least 50% of the the incident ultraviolet radiation by the stabilizer coating composition.

Absorbance is calculated using the equation $$A = \log\left(\frac{I_0}{I}\right)$$

in which A is the absorbance, $I_o$ is the intensity of the incident light and I is the intensity of the transmitted light.

The stabilizing coating solution compositions, i.e., the coating material, UV stabilizer, any other additives, and solvent contain from about 1 to about 40 weight percent UV absorber based on the weight of polymer solids in the composition and preferably from about 8 to about 30 weight percent based on polymer solids in the composition. The coating may contain a single ultraviolet radiation absorbing compound or a combination of one or more ultraviolet radiation absorbing compounds. Light stabilization compositions having higher concentrations of UV absorber than mentioned above are useful in the practice of the present invention and are within the full intended scope of the invention.

The UV absorber is applied to the plastic substrate or article in a coating composition. It is important that the coating composition adhere to the surface and not adversely affect the underlying plastic properties such as by stress cracking or crazing, crack propagation reducing impact resistance and tensile strength.

The use of ultraviolet radiation absorbers with various resins such as polycarbonates, polyesters, polyolefins, polystyrene, and vinyls to protect against attack by ultraviolet radiation is known in the art. The ultraviolet radiation absorber functions by reason of its ability to screen out the damaging portion of the incident radiation due to a high absorbtivity relative to that of the polymer. In order to qualify as a successful ultraviolet light absorber there are several requirements which must be met. The absorber must have a high specific absorbtivity in the range of wavelengths that are most deliterious to the underlying plastic substrate or article. The absorber must be compatible with the polymer and the coating composition. In addition the absorber should not significantly absorb in the visible region of the spectrum or a color will be imparted to the underlying substrate or article.

Those skilled in the art will gain a further and better understanding of the present invention from the detailed description set forth below, considered in conjunction with the examples and chemical drawings accompanying and forming a part of the specification.

EXAMPLE 1

Preparation of compound I—2-(Methyl Oxirane)-4, 6-Dibenzoyl Resorcinol 5.6 mmol, (2 g) of 2-allyl-4,6-dibenzolyresorcinol and 11 mmol, (0.8 g) of ~50% active meta-chloroperbenzoic acid were dissolved in toluene at room temperature. The reaction proceeded for 1 hr. The reaction mixture was washed three times with ~50 mL sodium bicarbonate/water. The toluene fraction was then evaporated to dryness. The resulting yellow-white solid was dried in a vacuum oven at 50° C. overnight. Yield 99% The ¹HNMR (300 MHz, CDCl₃):2.7 ppm (dd, 1 H); 2.8 ppm (dd, 1 H); 2.9 ppm (dd, 1 H); 3.0 ppm (dd, 1 H); 3.3 ppm (quintuplet, 1 H). FD-MS showed a parent ion with m/z 374, as calculated for this structure.

EXAMPLE 2

Preparation of compound IIA & IIB 1.3 mmol, (0.5 g) of 2(methyloxirane)-4,6-dibenzoyl resorcinol was dissolved in 10 mL of methanol/methylene chloride solution. The pH was adjusted to 1–2 with concentrated sulfuric acid. The solution was refluxed for 1 hr. The product was then extracted with methylene chloride. The methylene chloride was then evaporated to dryness leaving behind a whitish-yellow product. The product was dried in a vacuum oven overnight. The NMR and FD-MS (m/z 407) confirmed the product as a mixture of isomers (4:1 ratio, undefined).

EXAMPLE 3

Preparation of compound III 1.3 mmol, 0.5 g of 2-(methyloxirane)-4,6-dibenzoylresorcinol and 1.3 mmol 0.3 g of 25% sodium methoxide in methanol were combined in a solution of methanol, water and 5 drops of sulfuric acid at room temperature for 5 hr. Upon completion of the reaction, methylene chloride was added to extract the product. The methylene chloride fraction was then evaporated to dryness yielding a white solid. Crude yield 98%. The NMR (300 MHz, CDCl₃):3.15 ppm (dd, 1 H); 3.3 ppm (dd, 1 H); 3.75 ppm (dd, 1 H); 3.9 ppm (dd, 1 H); 5.2 ppm (quintuplet, 1 H). FD-MS (m/z 374) confirmed the structure of the product.

EXAMPLE 4

Preparation of compound V 5.3 mmol, 2.0 g of 2-(methyloxirane)4,6-dibenzoylresorcinol, 5 drops of sulfuric acid and less than 1 mL of water were combined in acetone and allowed to stir at 50° C. for 5 hr. The solution was filtered to collect the precipitate, washed with isopropanol and dried in a 50° C. vacuum oven for 4 hr. Crude yield 1.6 g (66.7%). The NMR (300 MHz, CDCl₃):1.45 ppm (d, 6 H); 3.0, 3.3 ppm (dd, 2 H); 3.9,4.1 ppm (dd, 2 H); 4.6 ppm (quintuplet, 1 H). FD-MS (m/z 431) confirmed the structure of the product.

EXAMPLE 5

Preparation of compound IV 3.7 mmol (1.6 g) of compound V, 10 drops of sulfuric acid and ~1 mL of water were combined in isopropanol and allowed to stir at 100° C. for one hour. Water was then used to precipitate the product. The product was then filtered to yield a yellowish-white solid product. Crude yield 1.3 g (89%). The NMR (300 MHz, CDCl₃):3.1 ppm (dd, 2 H); 3.6 ppm (dd, 2 H); 4.8 ppm (quintuplet, 1 H). FD-MS (m/z 392) confirmed the structure of the product.

Preparation of Films for Xenon Arc Accelerated Testing

A 5.33 g portion of Elvacite® 2041 (PMMA) was dissolved in 80.5 g of 2-methoxypropanol and 14.29 of diacetone alcohol at 50° C. in a three neck flask equipped with a mechanical stirrer and heating mantle. A 25 g aliquot of the polymer solution and 0.07 g of UV absorber were combined to make a solution containing 5 wt. % UV absorber based on PMMA solids. The prepared solutions were rotated on a roll mill overnight to allow the UV absorber to dissolve.

The solutions were then flow coated onto unstabilized 15 mil Lexan® film at 22° C. and 50% relative humidity. A 15 minute solvent flash was allowed before the films were baked in a 105° C. oven for 30 minutes.

The xenon arc accelerated testing was performed on a Ci35a xenon arc weather-ometer® using type S borosilicate inner and outer filters. The irradiance level was 0.77 W/m² at 340 nm, the black panel temperature was between 70–73° C., the dry bulb temperature was 450° C. with a wet bulb depression of 10° C. (50% relative humidity). The cycle was 160 min. light, 5 minutes dark, 15 minutes dark with water spray. This cycle accumulates 2.46 KJ/m² at 340 nm per hour of operation. Samples were exposed for 420 hr under these conditions.

The color measurements are taken using a Gardner XL-835 colorimeter. These measurements are reported as delta YI.

| Sample | Final delta YI |
|---|---|
| Compound I | 2.9 |
| Compound IIA & IIB | 2.7 |
| Compound III | 3.3 |
| Compound IV | 2.5 |
| Compound V | 1.9 |
| Control (PMMA Coated PC Film) | 7.0 |

What is claimed:

1. A compound having the formula

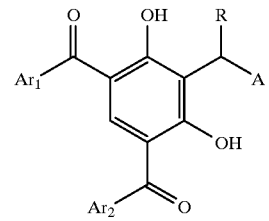

where $Ar_1$ and $Ar_2$ are independently substituted or unsubstituted monocyclic or polycyclic aryl groups, R is hydrogen, or an aliphatic group having from 1 to 8 carbon atoms, and A is

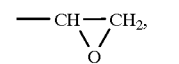

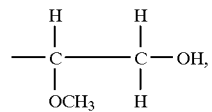

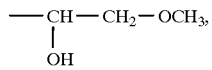

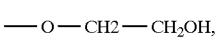

-continued

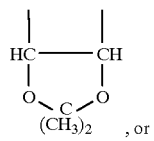
, or

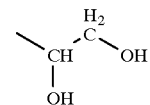

2. A compound according to claim 1 having the formula

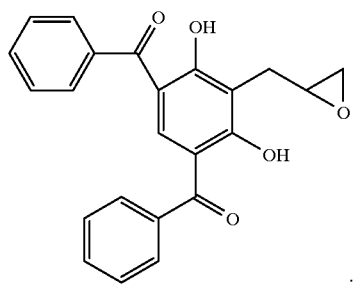

3. A compound according to claim 1 having the formula

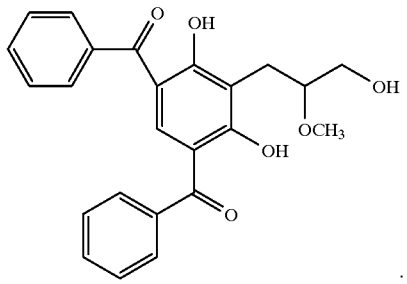

4. A compound according to claim 1 having the formula

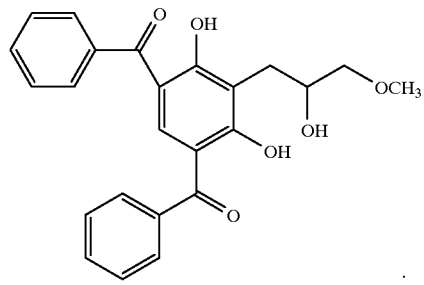

5. A compound according to claim 1 having the formula

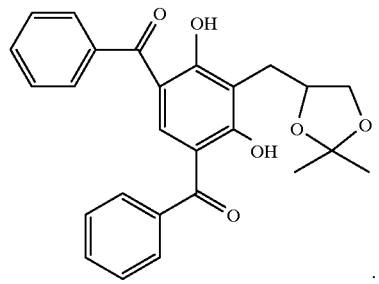

6. A compound according to claim 1 having the formula

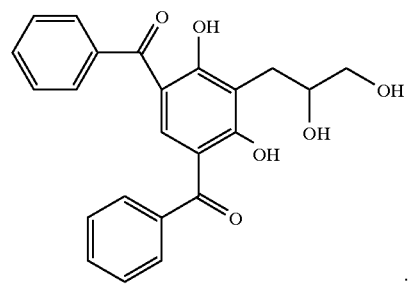

7. A compound having the formula

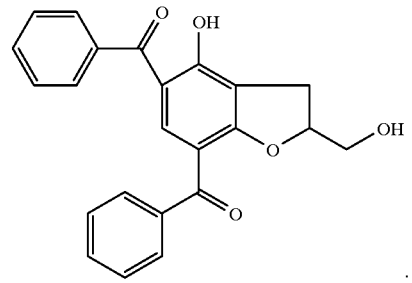

8. A UV absorbing coating composition comprising a transparent thermoplastic or thermosetting polymeric matrix material and a UV absorbing compound selected from the group consisting of 2-(methyloxirane)-4,6-dibenzoylrescorcinol, 2-(3-hydroxy-2-methoxypropyl)-4,6-dibenzoylresorcinol, 2-(2-hydroxy-3-methoxypropyl)-4,6-dibenzoylresorcinol, 2-hydroxymethyl-5-hydroxy-6,8-dibenzoyl-2,3-dihydrobenzofuran, 2-(2,3-dihydroxypropyl)-4.6-dibenzoylresorcinol, and 2,2-dimethyl-5-[(2,6-dihydroxy-3,5-dibenzoylphenyl)methyl]-1,3-dioxolane.

9. A UV absorbing coating composition according to claim 8 comprising a transparent matrix material and 2-(methyloxirane)-4,6-dibenzoyl rescorcinol.

10. A UV absorbing coating composition according to claim 8 comprising a transparent matrix material and 2-(3-hydroxy-2-methoxypropyl)-4,6-dibenzoylresorcinol.

11. A UV absorbing coating composition according to claim 8 comprising a transparent matrix material and 2-(2-hydroxy-3-methoxypropyl)-4,6-dibenzoylresorcinol.

12. A UV absorbing coating composition according to claim 8 comprising a transparent matrix material and 2-(2,3-dihydroxypropyl)-4,6-dibenzoylresorcinol.

13. A UV absorbing coating composition according to claim 8 comprising a transparent matrix material and 2,2-dimethy-5-[(2,6-dihydroxy-3,5-dibenzoylphenyl)methyl]-1,3-dioxolane.

14. A UV absorbing coating composition comprising a transparent thermoplastic or thermosetting polymer matrix material and 2-hydroxymethyl-5-hydroxy-6,8-dibenzoyl-2,3-dihydrobenzofuran.

15. A coated article comprising a solid substrate and coating on the surface thereof comprising a thermoplastic or thermosetting transparent matrix material and a UV absorbing compound selected from the group consisting of 2-(methyloxirane)-4,6-dibenzoylrescorcinol, 2-(3-hydroxy-2-methoxypropyl)-4,6-dibenzoylresorcinol, 2-(2-hydroxy-3-methoxypropyl)-4,6-dibenzoylresorcinol, 2-hydroxymethyl-5-hydroxy-6,8-dibenzoyl-2,3-dihydrobenzofuran, 2-(2,3-dihydroxypropyl)-4,6-dibenzoylresorcinol, and 2,2-dimethyl-5-[(2,6-dehydroxy-3,5-dibenzoylphenyl)methyl]-1,3-dioxolane.

* * * * *